United States Patent
Tameishi et al.

(10) Patent No.: US 11,166,859 B2
(45) Date of Patent: *Nov. 9, 2021

(54) METHOD OF MAKING WEARABLE ARTICLE COMPRISING ELASTIC BELT

(71) Applicant: The Procter & Gamble Company, Cincinnati, OH (US)

(72) Inventors: Kazuaki Tameishi, Kobe (JP); DonSub Lee, Akashi (JP); Fumitake Yamashita, Kobe (JP); Ying Jia, Beijing (JP)

(73) Assignee: The Procter & Gamble Company, Cincinnati, OH (US)

( * ) Notice: Subject to any disclaimer, the term of this patent is extended or adjusted under 35 U.S.C. 154(b) by 71 days.

This patent is subject to a terminal disclaimer.

(21) Appl. No.: 16/420,213

(22) Filed: May 23, 2019

(65) Prior Publication Data

US 2019/0274893 A1    Sep. 12, 2019

Related U.S. Application Data

(63) Continuation of application No. PCT/CN2016/107182, filed on Nov. 25, 2016.

(51) Int. Cl.
*A61F 13/496* (2006.01)
*B32B 37/00* (2006.01)
(Continued)

(52) U.S. Cl.
CPC .. *A61F 13/49011* (2013.01); *A61F 13/15593* (2013.01); *A61F 13/15804* (2013.01);
(Continued)

(58) Field of Classification Search
None
See application file for complete search history.

(56) References Cited

U.S. PATENT DOCUMENTS

2006/0030831 A1    2/2006    Matsuda et al.
2011/0094661 A1*   4/2011    Thorson ............ A61F 13/15585
                                                    156/211
(Continued)

FOREIGN PATENT DOCUMENTS

JP    2008229187 A    10/2008
JP    2016054989 A    4/2016
WO    2016029370 A1    3/2016

OTHER PUBLICATIONS

European Search Report dated Jan. 25, 2018.
International Search Report and Written Opinion; Application Ser. No PCT/CN2016/107182, dated Aug. 15, 2017, 9 pages.

*Primary Examiner* — Linda L Gray
(74) *Attorney, Agent, or Firm* — Charles R. Matson; Richard L. Alexander

(57) ABSTRACT

Disclosed is a method of manufacturing a wearable article assembled by a front belt, a back belt, and a central chassis, the central chassis having a front waist region and a back waist region separated from each other by a crotch region, wherein at least one of the front belt and the back belt is formed by an elastic belt, the method may comprise making the elastic belt and joining to the central chassis by the steps of: 1) advancing a first layer of continuous sheet having a first surface and an opposing second surface in a machine direction and defining a width in a cross machine direction; 2) advancing a second layer of continuous sheet having a first surface and an opposing second surface in the machine direction and having a smaller width than the first layer of continuous sheet; 3) advancing a first group of elastic bodies in the machine direction in a stretched state; 4) joining the first group of elastic bodies between the first surface of the first layer and the first surface of the second layer of continuous sheets to form a primary elastic belt precursor; 5) advancing a second group of elastic bodies in the machine (Continued)

direction in a stretched state; 6) joining the second group of elastic bodies to the first surface of the first layer of continuous sheet of the primary elastic belt precursor; 7) joining the central chassis to the second surface of the second layer of continuous sheet; and 8) folding the first layer of continuous sheet to form a first layer fold over of continuous sheet, such that at least one of the second group of elastic bodies is directly joined between the first surface of the first layer of continuous sheet and the first surface of the first layer fold over of continuous sheet.

9 Claims, 11 Drawing Sheets

(51) Int. Cl.
*B32B 5/12* (2006.01)
*B32B 5/24* (2006.01)
*B32B 3/04* (2006.01)
*A61F 13/00* (2006.01)
*B32B 43/00* (2006.01)
*A61F 13/49* (2006.01)
*A61F 13/15* (2006.01)
*B32B 37/14* (2006.01)

(52) U.S. Cl.
CPC ...... *A61F 13/496* (2013.01); *A61F 13/49009* (2013.01); *A61F 13/49012* (2013.01); *A61F 13/49015* (2013.01); *B32B 3/04* (2013.01); *B32B 5/12* (2013.01); *B32B 5/24* (2013.01); *B32B 37/144* (2013.01); *B32B 43/003* (2013.01); *Y10T 156/101* (2015.01); *Y10T 156/1011* (2015.01); *Y10T 156/1034* (2015.01); *Y10T 156/1043* (2015.01); *Y10T 156/1049* (2015.01); *Y10T 156/1051* (2015.01); *Y10T 156/1084* (2015.01)

(56) References Cited

U.S. PATENT DOCUMENTS

| | | |
|---|---|---|
| 2013/0211357 A1 | 8/2013 | Nishikawa et al. |
| 2013/0317471 A1 | 11/2013 | Morimoto et al. |
| 2014/0000794 A1 | 1/2014 | Hamilton |
| 2014/0074642 A1 | 3/2014 | Brookmeyer |
| 2016/0128874 A1 | 5/2016 | Schneider et al. |
| 2017/0165129 A1 | 6/2017 | Morimoto et al. |

* cited by examiner

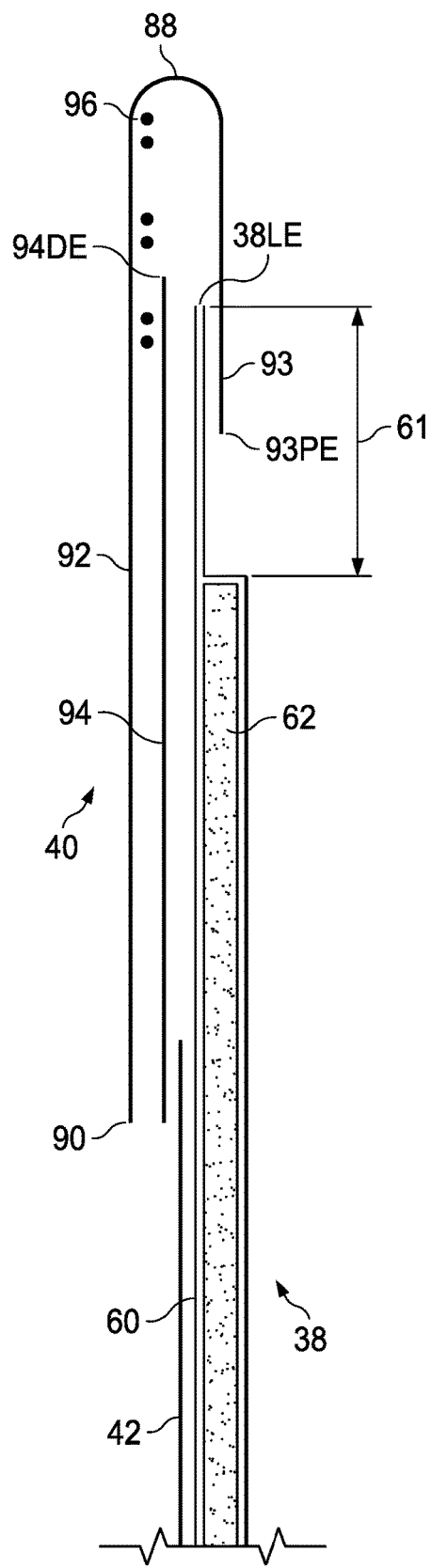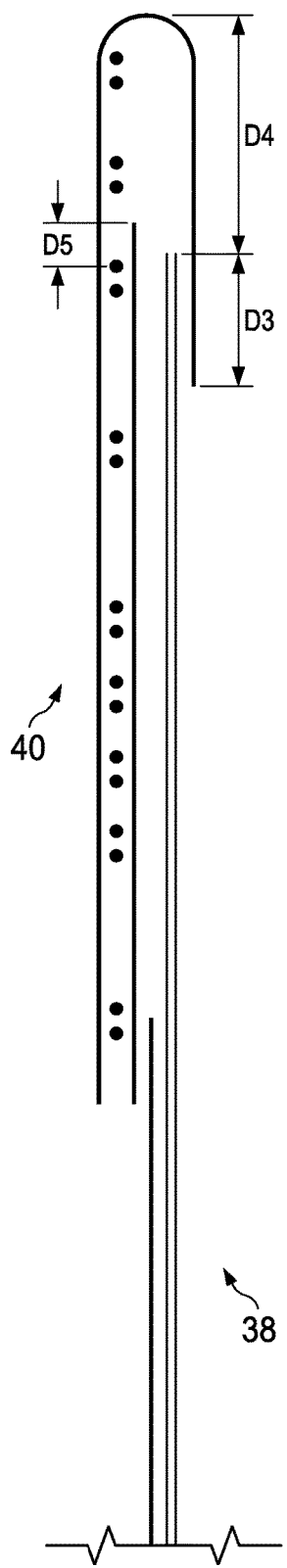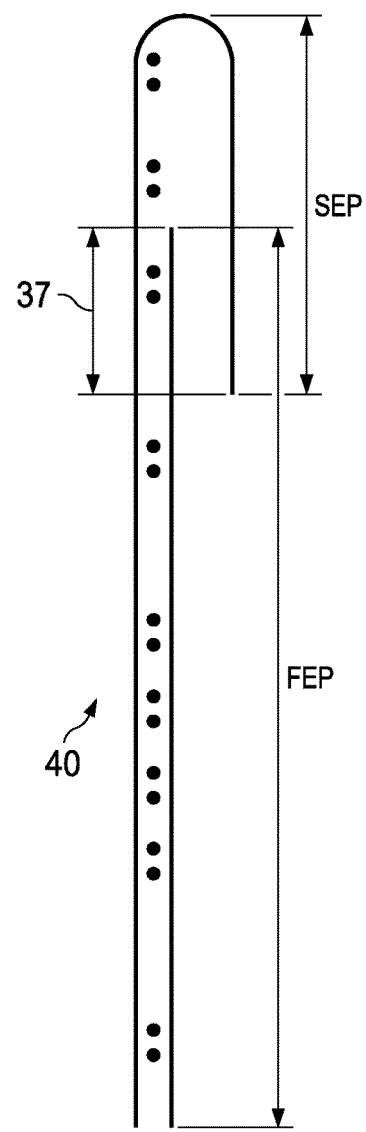
FIG. 3A
FIG. 3B
FIG. 3C

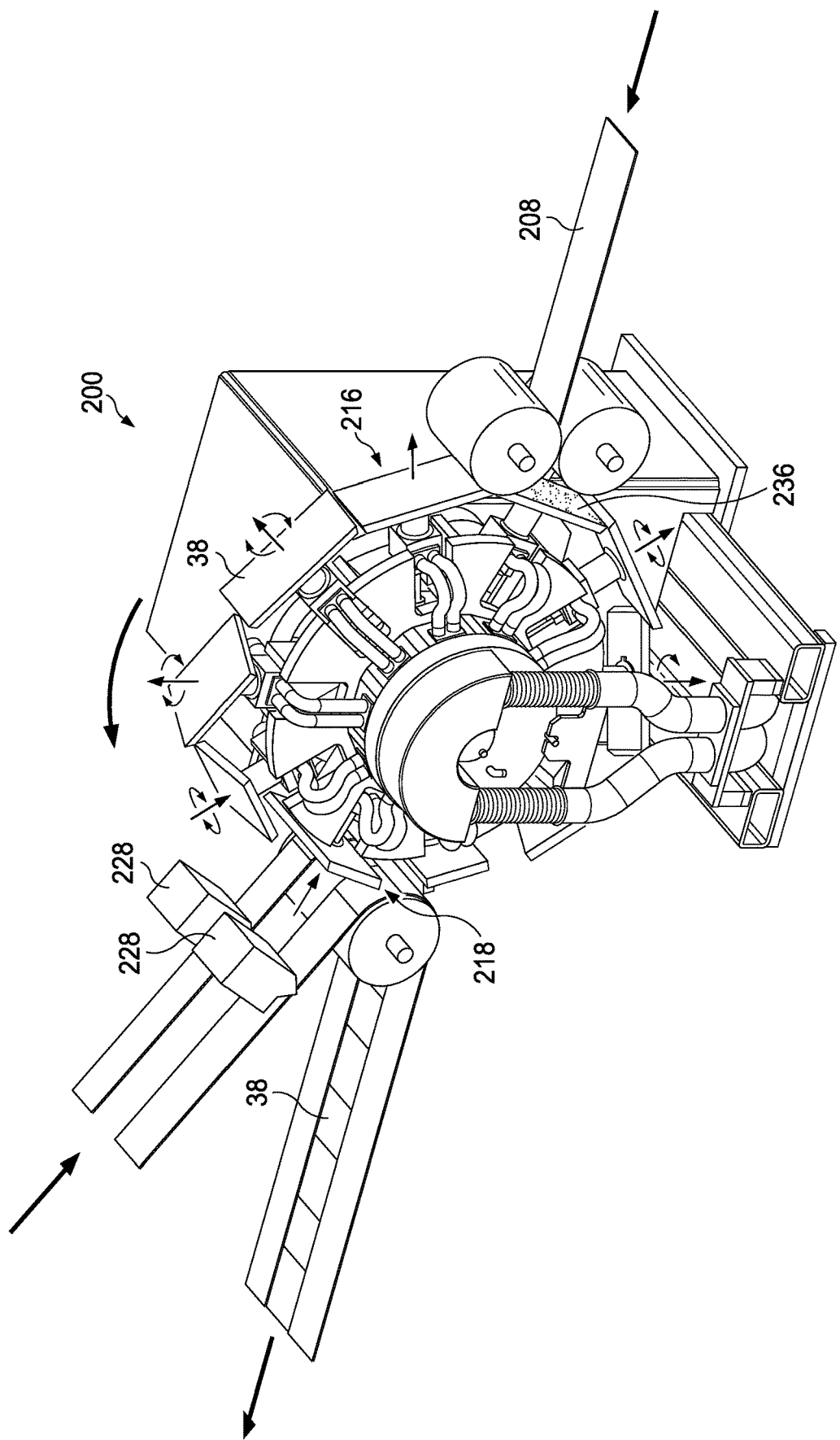

METHOD OF MAKING WEARABLE ARTICLE COMPRISING ELASTIC BELT

CROSS REFERENCE TO RELATED APPLICATION

This application is a continuation, and claims priority under 35 U.S.C. § 120, to Patent Application No. PCT/CN2016/107182, filed on Nov. 25, 2016, the entire disclosure of which is hereby incorporated by reference.

FIELD OF THE INVENTION

The present invention relates to a method of making a wearable article comprising an elastic belt, and articles made thereof.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult.

Belt-type pants having a main body to cover the crotch region of the wearer and a separate elastic belt defining the waist opening and leg opening are known in the art, such as described in PCT Publication WO 2006/17718A. Such belt-type pants have an elastic belt made of a laminate of 2 substrate layers and elastic bodies sandwiched therebetween. These elastic belts may be economically made by joining the elastic bodies to one of such substrate layers, overlaying and joining the other substrate layer on top to make a laminate, and then deactivating the elastic bodies in certain regions to, for example, avoid having elasticity where the elastic belt would overlap the absorbent core. While such method of making the elastic belt may be conveniently conducted by joining and deactivating all of the elastic bodies of the laminate concurrently, this may not be effective or provide the best results when different force or tactile sense is desired for different portions of the belt. Further, when the laminate is made of 2 layers of substrates, one of the layers may be folded over to avoid having sharp edges at the waist opening or the leg opening. Such a configuration results in regions that are provided in 3 layers and 2 layers. The resulting difference in layers may provide disadvantages such as non-uniform gathering to the laminate, less controllable force profile, or undesirable tactile sense. There may be interest to decrease or eliminate such difference of layers, or to provide a construction wherein the differing layers provide specific functions.

Based on the foregoing, there is a need for a method of making a wearable article comprising an elastic belt with various belt configurations in an effective and economical manner.

SUMMARY OF THE INVENTION

The present invention is directed to a method of manufacturing a wearable article assembled by a front belt, a back belt, and a central chassis, the central chassis having a front waist region and a back waist region separated from each other by a crotch region; wherein at least one of the front belt and the back belt is formed by an elastic belt, the method comprising making the elastic belt and joining to the central chassis by the steps of;

advancing a first layer of continuous sheet having a first surface and an opposing second surface in a machine direction and defining a width in a cross machine direction;

advancing a second layer of continuous sheet having a first surface and an opposing second surface in the machine direction and having a smaller width than the first layer of continuous sheet;

advancing a first group of elastic bodies in the machine direction in a stretched state;

joining the first group of elastic bodies between the first surface of the first layer and the first surface of the second layer of continuous sheets to form a primary elastic belt precursor advancing a second group of elastic bodies in the machine direction in a stretched state; joining the second group of elastic bodies to the first surface of the first layer of continuous sheet of the primary elastic belt precursor;

joining the central chassis to the second surface of the second layer of continuous sheet;

folding the first layer of continuous sheet to form a first layer fold over of continuous sheet, such that at least one of the second group of elastic bodies is directly joined between the first surface of the first layer of continuous sheet and the first surface of the first layer fold over of continuous sheet.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

FIG. 3A is a schematic cross section view of FIG. 2 taken along line L1 in one embodiment of belt structure, either on the front belt or the back belt.

FIG. 3B is a schematic cross section view of FIG. 2 taken along line L2 in one embodiment of belt structure, either on the front belt or the back belt.

FIG. 3C is a schematic cross section view of FIG. 2 taken along line L3 in one embodiment of belt structure, either on the front belt or the back belt.

FIG. 12 is a schematic view of the central chassis forming and joining step of the process of the present invention.

DEFINITIONS

Figure 1:
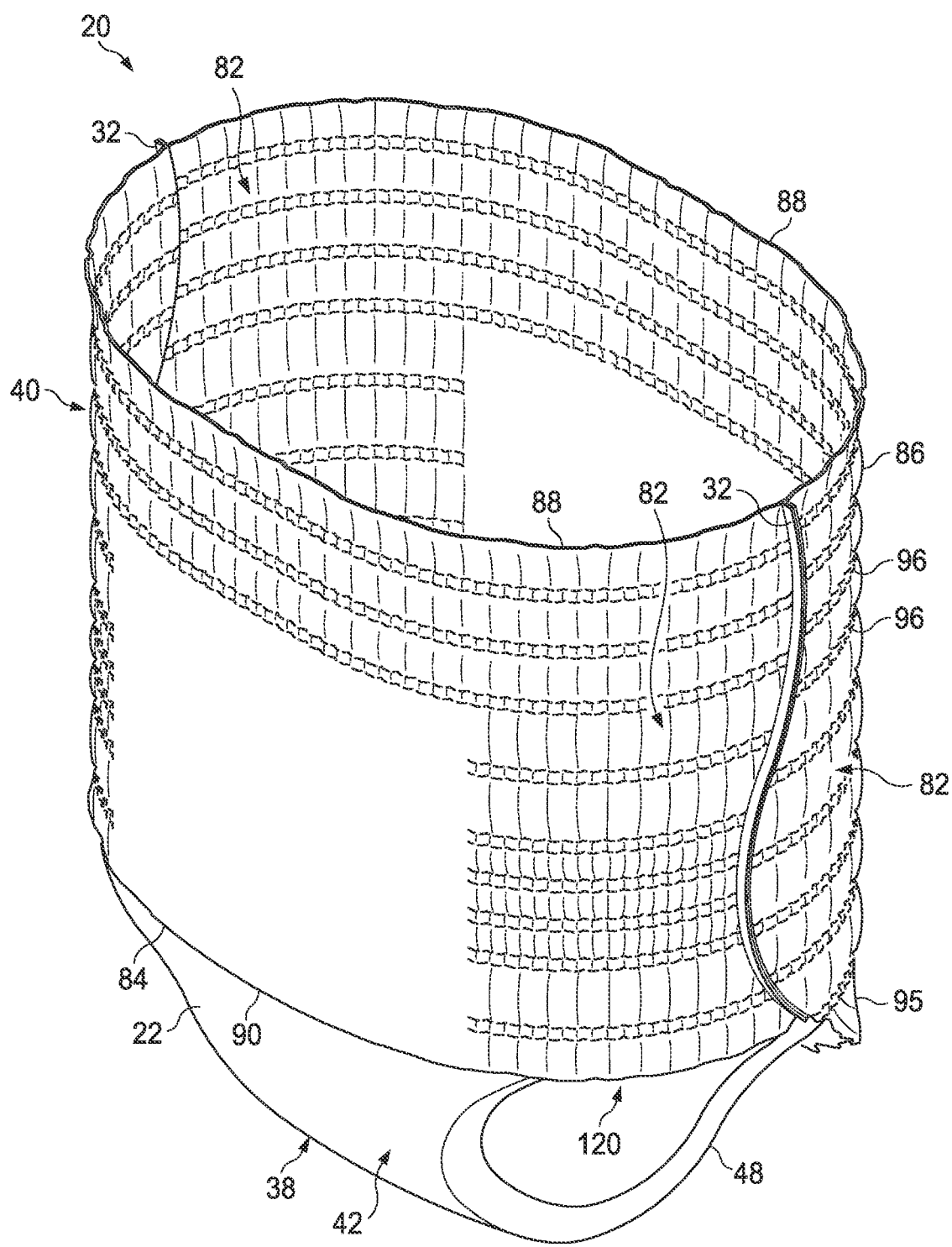
FIG. 1 is a perspective view of one embodiment of a wearable article of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article. "Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element. Joining may be provided by applying adhesive agents, ultrasound or by embossing the at least two elements to be affixed to one another.

"Proximal" refers to a portion being closer or planned to be closer relative to the longitudinal center of the article, while "distal" refers to a portion being farther or planned to be farther from the longitudinal center of the article.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF THE INVENTION

Figure 2:
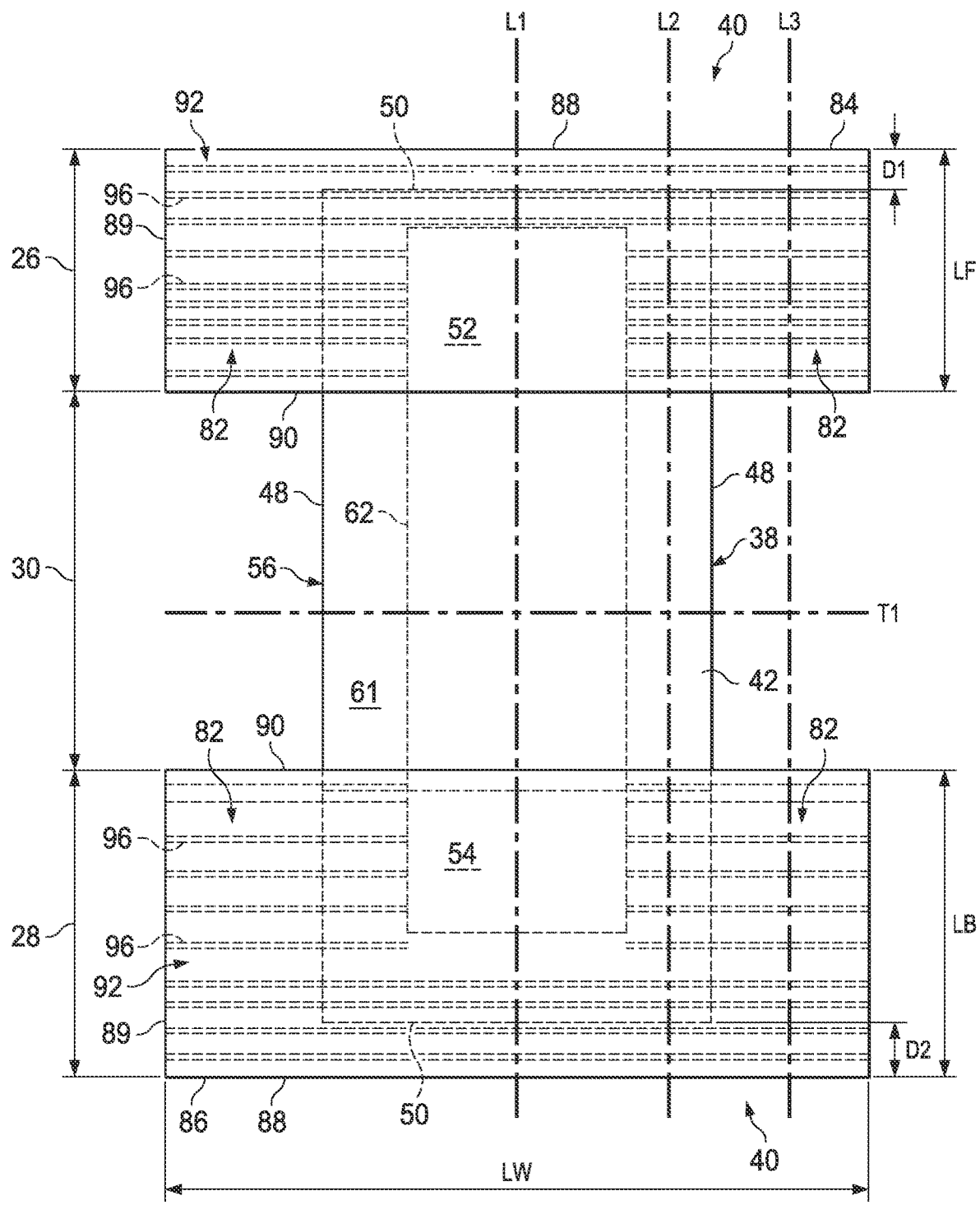
FIG. 2 is a schematic plan view of one embodiment of a wearable article of the present invention with the seams unjoined and in a flat uncontracted condition showing the garment facing surface.

FIG. 1 is a perspective view of an embodiment of the wearable article 20 made by the present invention and FIG. 2 is a schematic plan view of the same article with the seams unjoined and in its flat uncontracted condition showing the garment-facing surface. In FIGS. 1 and 2, the position of the elastics 96 may or may not be accurate. The wearable article 20 has a longitudinal centerline L1 which also serves as the longitudinal axis, and a transverse centerline T1 which also serves as the transverse axis. The wearable article 20 has a body facing surface, a garment facing surface, a front region 26, a back region 28, a crotch region 30, and seams 32 which join the front region 26 and the back region 28 to form two leg openings and a waist opening. The wearable article 20 comprises a center chassis 38 to cover the crotch region of the wearer, a front belt 84 and a back belt 86 (hereinafter may be referred to as "front and back belts"), the front and back belts 84, 86 forming a ring-like elastic belt 40 (hereinafter may be referred to as "waist belt") extending transversely defining the waist opening. The front and back belts 84, 86 and the center chassis 38 jointly define the leg openings.

Figure 4:
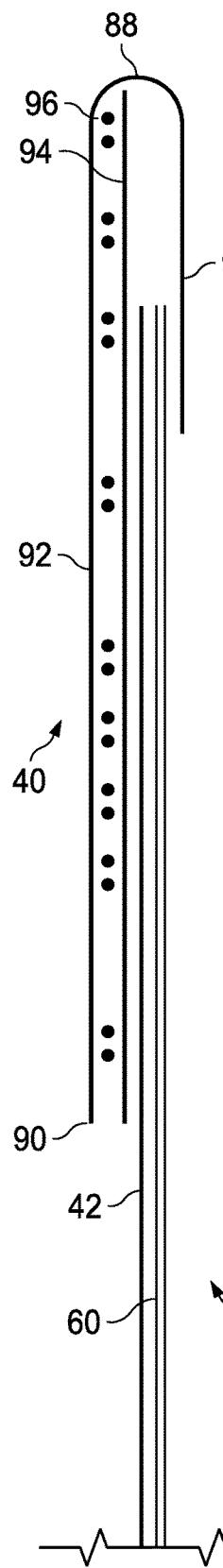
FIG. 4 is a schematic cross section view of a wearable article of the prior art.
Figure 5:
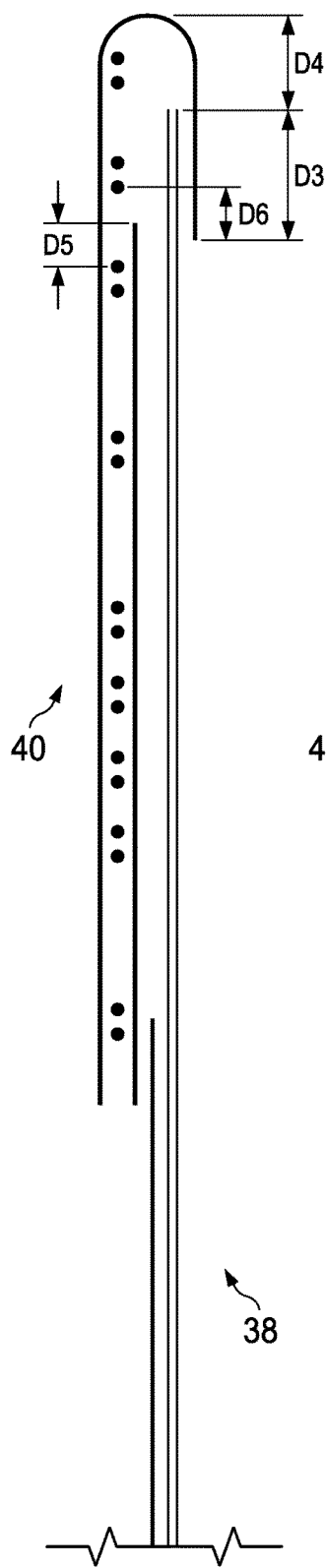
FIG. 5-7 are schematic cross section views of FIG. 2 taken along line L2 in other embodiments of belt structure, either on the front belt or the back belt.
Figure 6:
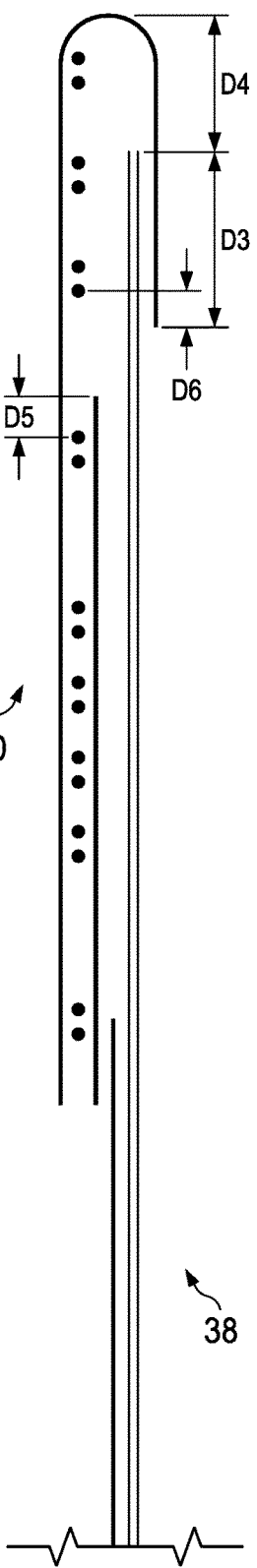
Figure 7:
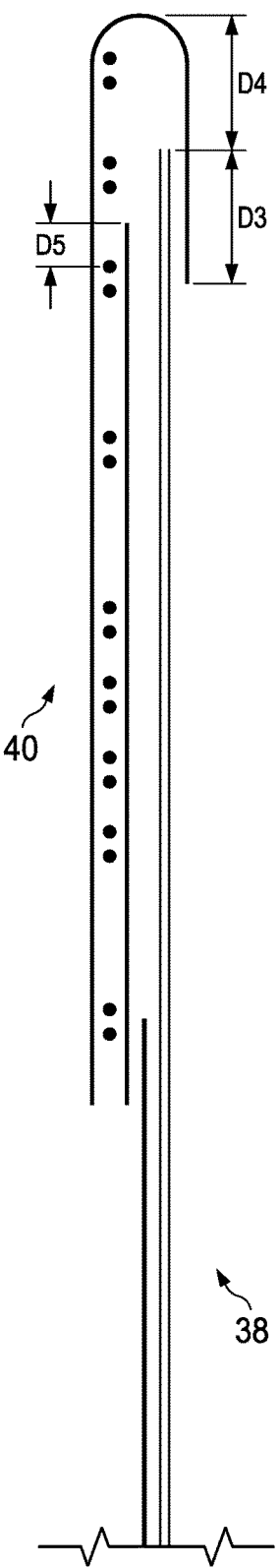

FIGS. 3A, 3B, and 3C are schematic cross section views of one embodiment article made by the present invention, taken along lines L1, L2, and L3, respectively. L1 describes the longitudinal centerline, while L2 describes a longitudinal line running through the transverse edge of the center chassis 38, and L3 describes a longitudinal line running through the left and right panels 82 where the center chassis 38 does not exist. FIG. 4 is a schematic cross section view of the prior art taken along L2 of a belt-type pant article. FIG. 5-7 is a schematic cross section view of other article embodiments made by the present invention taken along L2. In FIGS. 3A-C, and 4-7, the thickness dimension may be exploded and exaggerated.

Referring to FIG. 3A, the center chassis 38 comprises a backsheet 60 and outer cover layer 42 for covering the garment-facing side of the backsheet 60. The backsheet 60 may be a water impermeable film. The outer cover layer 42 may be a nonwoven sheet. The center chassis 38 may contain an absorbent material existing region 62 for absorbing and containing body exudates disposed on the center chassis 38, and an absorbent material non-existing region 61 surrounding the periphery of the absorbent material existing region 62. In the embodiment shown in FIG. 2, the center chassis 38 has a generally rectangular shape, left and right longitudinally extending side edges 48 (hereinafter may be referred to as "side edge") and front and back transversely extending end edges 50 (hereinafter may be referred to as "end edge"). The center chassis 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the center chassis 38, the center of the back belt 86 is joined to a back waist panel 54 of the center chassis 38, the front and back belts 84, 86 each having a left side panel and a right side panel 82 where the center chassis 38 does not overlap. The center chassis has a crotch panel 56 positioned between the front waist panel 52 and the back waist panel 54. The front and back belt are discontinuous of each other in the longitudinal direction.

Referring to FIGS. 1 and 2, the ring-like belt 40 formed by the front belt 84 and back belt 86 acts to dynamically create fitment forces and to distribute the forces dynamically generated during wear. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the center chassis 38. The front leg opening region 120 is disposed adjacent the leg opening along the proximal edge 90 of the left and right side panels 82 of the front belt 84.

The front belt 84 and back belt 86 are configured to impart elasticity to the belt 40. The front belt 84 and the back belt 86 may each be formed by a laminate comprising a plurality of elastic bodies 96 running in the transverse direction, an inner sheet 94, an outer sheet 92, and an outer sheet fold over 93 wherein the outer sheet fold over 93 is an extension of the outer sheet material formed by folding the outer sheet material at the distal edge 88 of the front and back belts; wherein the belt elastic bodies 96 are sandwiched between two of these sheets. The front belt 84 and the back belt 86 may each be made only by elastic bodies 96, the inner sheet 94, the outer sheet 92, and the outer sheet fold over 93. The outer sheet fold over 93 may be directly joined to the center chassis 38. The belt elastic bodies 96 may extend in the transverse direction to provide a ring like elastic belt 40 when the front belt 84 and the back belt 86 are joined. At least some of the elastic bodies 96 extend in the transverse direction substantially parallel to each other. All of the elastic bodies 96 may extend in the transverse direction substantially parallel to each other. Such an article may be economically made. The front and back belt 84, 86 each have transversely continuous proximal and distal edges, the proximal edge 90 being located closer than the distal edge 88 relative to the longitudinal center of the article. The outer sheet fold over 93 is an extension of the outer sheet material formed by folding the outer sheet material at the distal edge 88 of the front and back belts 84, 86. The elastic bodies 96 may be disposed in the same or different denier, interval, or force between the front and back, as well as in different longitudinal positions of the belt. The inner and outer sheets 92, 94 may be the same or different material, and selected to provide characteristics such as breathability, softness, cushiony feel, loftiness, and combinations thereof, depending on the desirables of the resulting article. The inner and outer sheets 92, 94 may have the same or different basis weight, stiffness, texture or any combination thereof.

Referring to FIG. 2, the transverse width LW of the back belt 86 in the uncontracted condition may be the same as the transverse width of the front belt 84 of the same condition. Such an article may be economically made.

The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such configuration, the seams 32 close the front and back belt 84, 86 side edges 89 of the same length for forming the article. Such an article may be economically made.

The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1 and 2). In such configuration, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the center chassis 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Articles known in the art such as in FIG. 4 have the longitudinal length of the inner sheet approximately matching the longitudinal length of the elastic belt. This provides regions of the elastic belt having 3 layers for a significant percentage of the belt while leaving the other regions in 2 layers.

Referring to FIGS. 3A-C, the present invention enables manufacturing of articles having a region towards the distal edge of the elastic belt 88 wherein the elastic belt 40 is made only by the outer belt 92, the outer belt fold over 93, and elastics 96 disposed therebetween. In FIGS. 3B-C, there are 4 elastic bodies 96 which are disposed between the outer belt 92 and the outer belt fold over 93, 2 elastic bodies 96 which are disposed where 3 layers overlap (outer belt 92, inner belt 93, and outer belt fold over 93), and 12 elastic bodies 96 which are disposed between the inner belt 94 and the outer belt 92. Namely, a majority of elastic bodies are disposed between 2 layers.

Referring to FIGS. 5-6, the present invention also enables manufacturing articles which have all of the elastic bodies 96 disposed in only 2 layers, namely either between the outer belt 92 and the outer belt fold over 93, or between the inner belt 94 and the outer belt 92.

Figure 8:
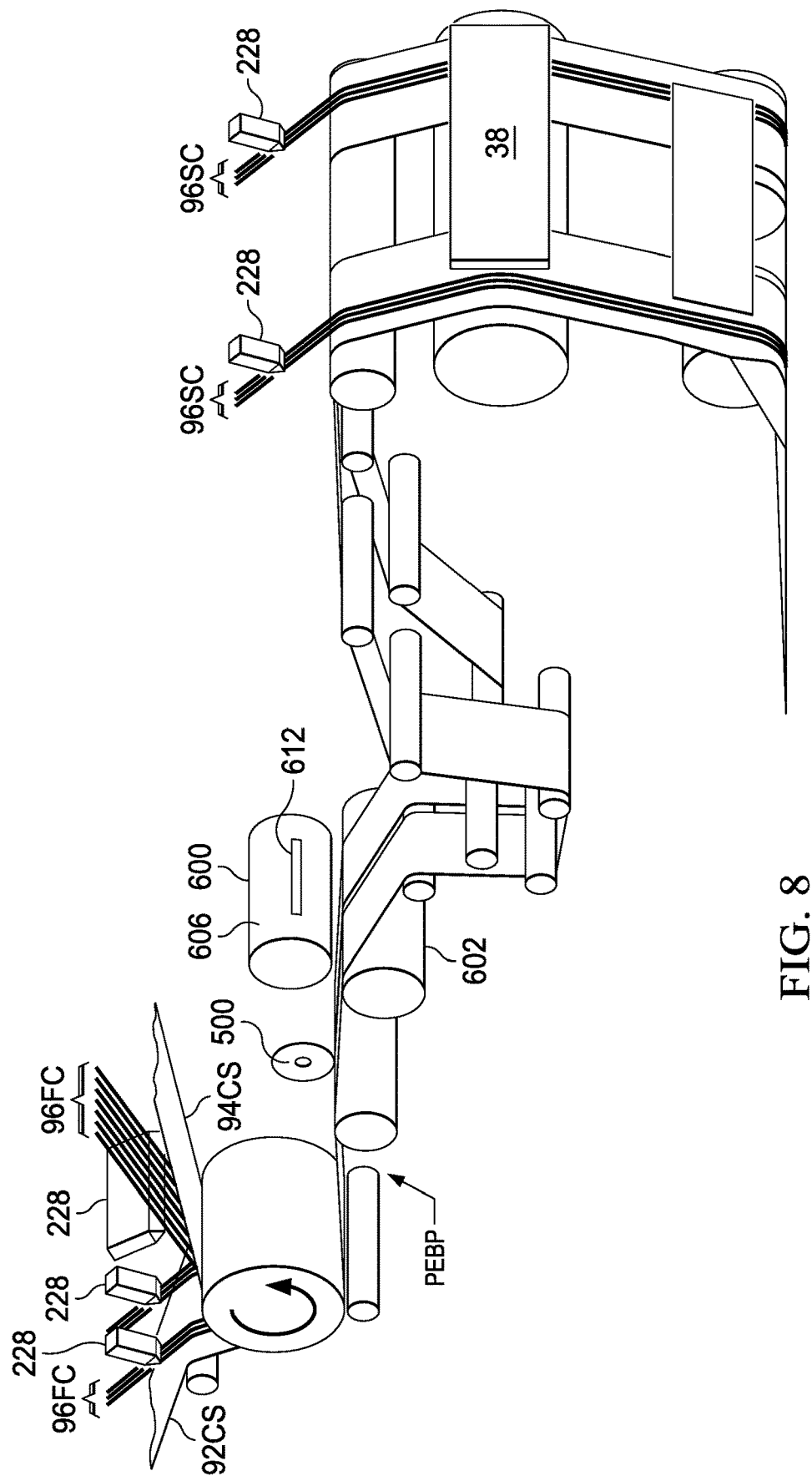
FIG. 8 is a schematic view of the process of the present invention.

Referring to FIG. 8, the present invention relates to making the elastic belt 40 and joining to the central chassis 38 by the following steps A)-D).

A) Related to forming a primary elastic belt precursor, or PEBP, the step comprising:
advancing a first layer of continuous sheet 92CS having a first surface and an opposing second surface in a machine direction and defining a width in a cross machine direction;
advancing a second layer of continuous sheet 94CS having a first surface and an opposing second surface in the machine direction and having a smaller width than the first layer of continuous sheet;
advancing a first group of elastic bodies 96FC in the machine direction in a stretched state;
joining the first group of elastic bodies 96FC between the first surface of the first layer and the first surface of the second layer of continuous sheets 92CS, 94CS, to form a PEBP.

B) Related to introducing the second group of elasic bodies 96SC comprising:
advancing a second group of elastic bodies 96SC in the machine direction in a stretched state;
joining the second group of elastic bodies 96SC to the first surface of the first layer of continuous sheet 92CS of the PEBP.

C) Related to joining the central chassis 38 to the second surface of the second layer of continuous sheet 94CS.

D) Related to folding the first layer to form a first layer fold over of continuous sheet 93CS, such that at least one of the second group of elastic bodies 96SC is directly joined between the first surface of the first layer of continuous sheet 92CS and the first surface of the first layer fold over of continuous sheet, 93CS.

In the finished article, the first layer of continuous sheet 92CS becomes the outer sheet 92 wherein the second surface of the first layer of continuous sheet 92CS becomes the garment facing surface, the second layer of continuous sheet 94CS becomes the inner sheet 94 wherein the second surface of the second layer of continuous sheet 94CS becomes the body facing surface, and the first layer fold over of continuous sheet 93CS becomes the outer sheet fold over 93 wherein the second surface of the first layer fold over of continuous sheet 93CS becomes the body facing surface.

Figure 16:
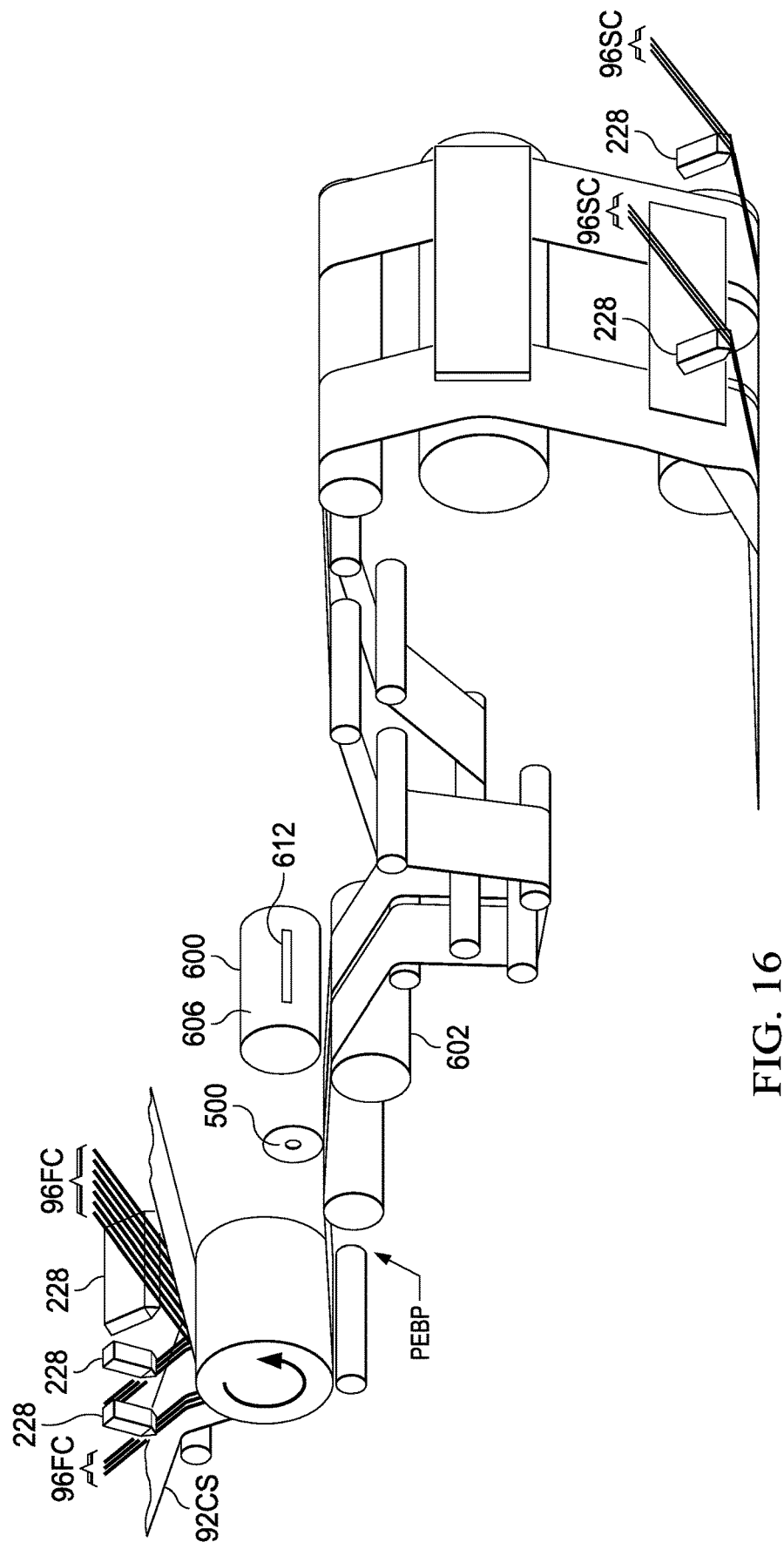
FIG. 16 is a schematic view of another process of the present invention.

FIG. 8 describes a schematic view of the entirety of the process of the present invention following the steps A)-D) in the order described above. Alternatively, steps B) and C) may be reversed, namely, the central chassis 38 may be joined to the PEBP prior to introducing the second group of elastic bodies 96SC on the proviso that, as seen in FIGS. 3A-C, there are no second group of elastic bodies 96SC planned to be disposed between the first layer of continuous sheet 93CS and the central chassis 38. Such alternative process is described in FIG. 16.

Step A)

Figure 9:
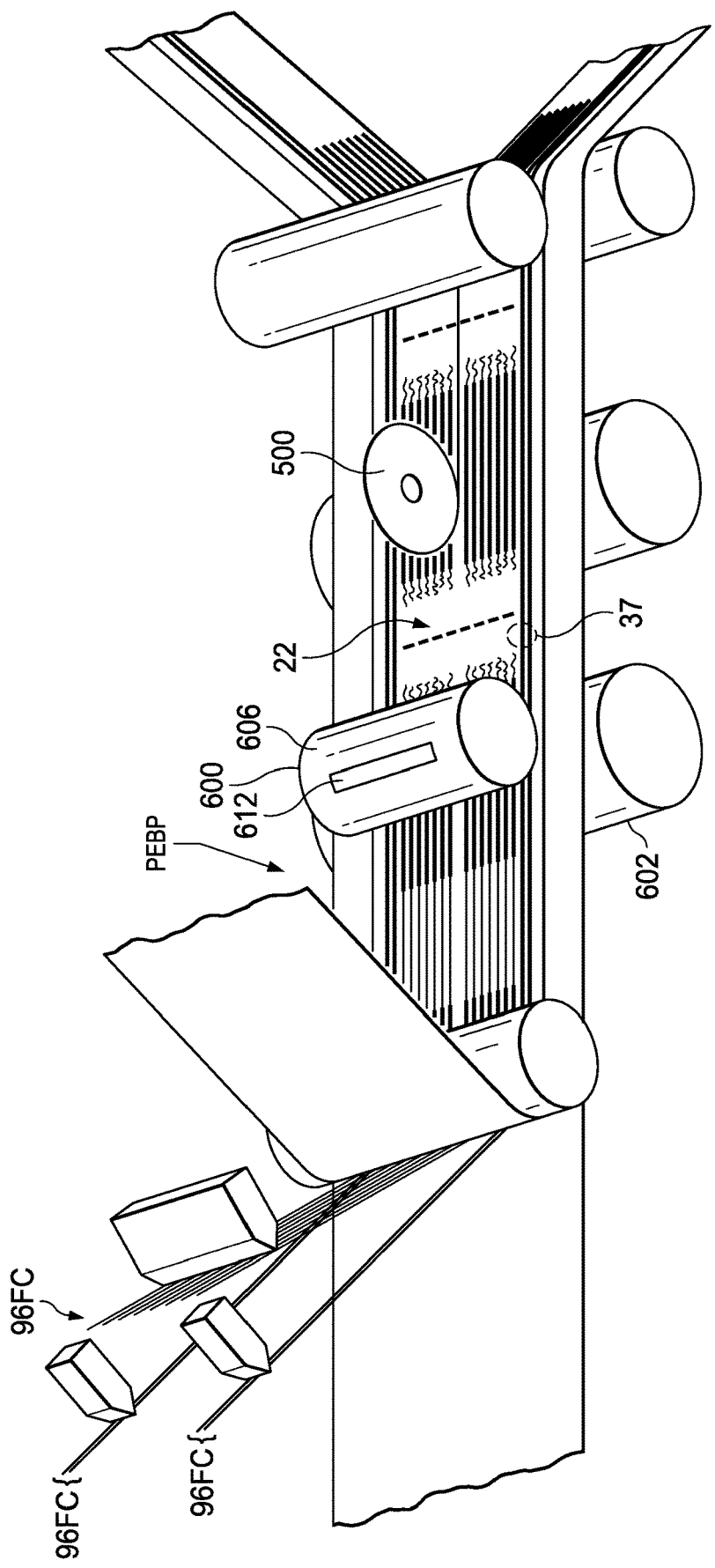
FIG. 9 is a schematic view of the primary elastic belt precursor forming step of the process of the present invention.

Referring to FIGS. 8 and 9, the PEBP forming step comprises advancing a first layer of continuous sheet 92CS having a first surface and an opposing second surface in a machine direction; advancing a second layer of continuous sheet 94CS having a first surface and an opposing second surface in the machine direction; advancing a first group of elastic bodies 96FC in the machine direction in a stretched state; and joining the first group of elastic bodies 96FC between the first surface of the first layer and the first surface of the second layers of continuous sheets 92CS, 94CS, to form a PEBP. The portion of the PEBP at which the first group of elastic bodies 96FC are joined may be referred to as the first elastic portion, or FEP.

In FIG. 9 the first group of elastic bodies 96FC are placed in the center in the cross machine direction of the first layer of continuous sheet 92CS on the proviso that the PEBP will later be divided into 2 continuous belt precursor parts for making the front belt and back belt, wherein one or both of the belts may be a PEBP made by the present process. In FIG. 9, the depictions after joining of the second layer of continuous sheet 94CS is shown as if the second layer of continuous sheet 94CS is removed and therefore the elastic bodies can be directly observed. The first and second layer of continuous sheets 94CS, 92CS have a width in a cross machine direction; wherein the second layer of continuous sheet 94CS has a smaller width than the first layer of continuous sheet 92CS to enable introducing the second group of elastic bodies 96SC in the later steps. The dimension of the second layer of continuous sheet 94CS and the positioning of first group of elastic bodies 96FC may be selected such that the elastic body closest to the edge of the second layer of continuous sheet 94CS is disposed at a distance D5 away from the edge of second layer of continuous sheet 94CS, wherein D5 may be at least about 5 mm. Referring to FIGS. 3B-C and 5-7, this may prevent any elastic body 96 from being accidentally left uncovered by the inner sheet 94 in the finished article. The elastic bodies 96 may be joined between the first and second layers of continuous sheets 92CS, 94CS by any means known in the art, including use of adhesive material dispensed by adhesive dispensers 228 immediately before joining.

The obtained PEBP may be divided by a slitter 500 in the machine direction to form 2 continuous parts, which are the front belt and the back belt precursors, wherein either or both of the front and back belt precursors are the PEBP according to the present invention. The dividing may be provided before or after making of the elastic region and non-elastic region 22 as described below.

Whether or not the front and back belt take the configurations of the present invention, the front belt precursor and the back belt precursor may be different in at least one of; the dimension of the precursor, the number of first group of elastic bodies, and the positioning of the first group of elastic bodies.

Referring to FIG. 8, the thus obtained FEP comprising: the lamination of the first and second layers of continuous sheets 92CS, 94CS and first group of elastic bodies 96FC; may comprise an elastic region and a non-elastic region 22. By elastic region, what is meant is a region which contributes to the elasticity of the waist belt 40 in the final article. By non-elastic region 22, what is meant is a region which does not contribute to the elasticity of the waist belt 40 in the final article. An elastic body unadhered to either of the first and second layers of continuous sheets 92CS, 94CS and cut in the unadhered area may be left dangling, thereby still exhibiting elasticity as an elastic body per se. However, so long as the elasticity is non-contributory to elasticity of the waist belt 40, such area is considered a non-elastic region 22. On the other hand, an elastic body unadhered to either or both of the first and second layers of continuous sheets 92CS, 94CS while continuing to exhibit elasticity is considered active in elasticity. Such area is considered an elastic region. Some of the first group of elastic bodies 96FC may be removed of its elasticity in regions planned to be joined to the transverse center of the central chassis 38, and then deactivating its elasticity to form a non-elastic region 22. Removal of elasticity from a certain area of the elastic belt 40 overlapping with the corresponding front and/or back waist panel 52, 54 may be advantageous when the center chassis 38 comprises an absorbent material existing region 62, in that elasticity in the front and/or back waist panel 52, 54 may cause bunching of the absorbent material existing region 62 and interfere with close fit of the center chassis 38 to the wearer.

Referring to FIGS. 8 and 9, the repetition of the elastic region and non-elastic region 22 on the FEP may be made by intermittently joining the first and second layers of continuous sheets 92CS, 94CS, followed by deactivating the elastic bodies disposed in the unjoined regions. The elasticity of the first group of elastic bodies 96FC may be removed by either leaving the elastic body unadhered to the first and second layers of continuous sheets 92CS, 94CS or adhering them to one or both of the first and second layers of continuous sheets 92CS, 94CS with significantly weaker adhesion than in the elastic region, and then deactivating the elastic bodies disposed in the unadhered or weakly adhered portion. A cutting unit may be employed for effective deactivation, and may be configured with a die knife, flexible blade, and/or compression roll features, and may also include additional features to control knife-anvil gaps and/or force, and may include means for heating. The cutting unit may include a cutting roll 600, an anvil roll 602, and a flexible blade 612 extending from the roll circumference surface 606 of the cutting roll 600.

All of the first group of elastic bodies 96FC may have a non-elastic region 22. Only a portion of the first group of elastic bodies 96FC may be provided with non-elastic regions 22, for example, those that are planned to be disposed closer to the proximal edge 90 of the resulting article. Accordingly, some of the first group of elastic bodies 96FC may be configured to remain elastic across the planned width of the elastic belt 40. The machine direction dimension of the non-elastic region 22 per elastic body may be varied.

Step B)

Figure 10:
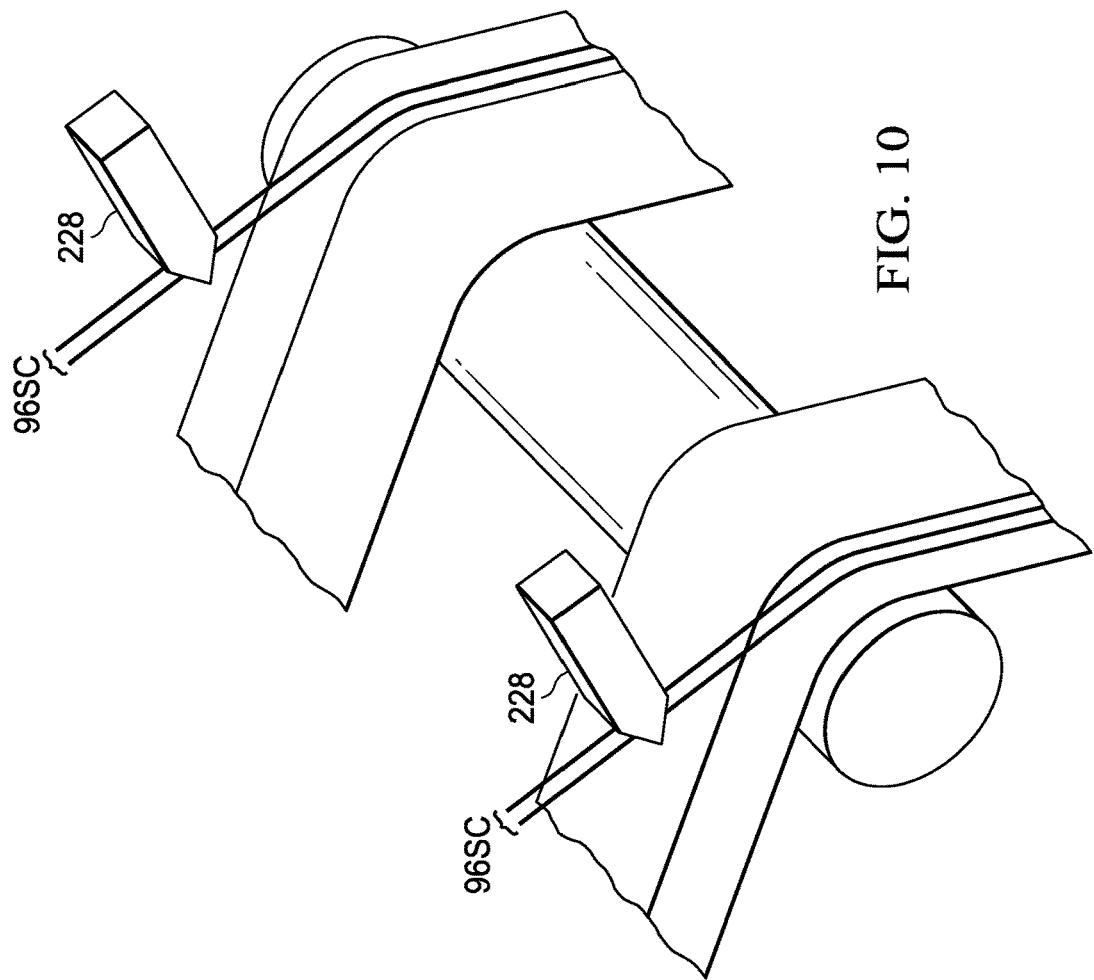
FIG. 10 is a schematic view of the second elastic introduction step of the process of the present invention.

Referring to FIGS. 8 and 10, the thus obtained PEBP is then sent to introduce the second group of elastic bodies 96SC comprising the steps of: advancing a second group of elastic bodies 96SC in the machine direction in a stretched state and joining the second group of elastic bodies 96SC to the first surface of the first layer of continuous sheet 92CS of the PEBP. The portion at which the second group of elastic bodies 96SC are joined may be referred to as the second elastic portion, or SEP. The SEP may be configured to be elastic across the planned width of the elastic belt 40.

Step C)

Figure 11:
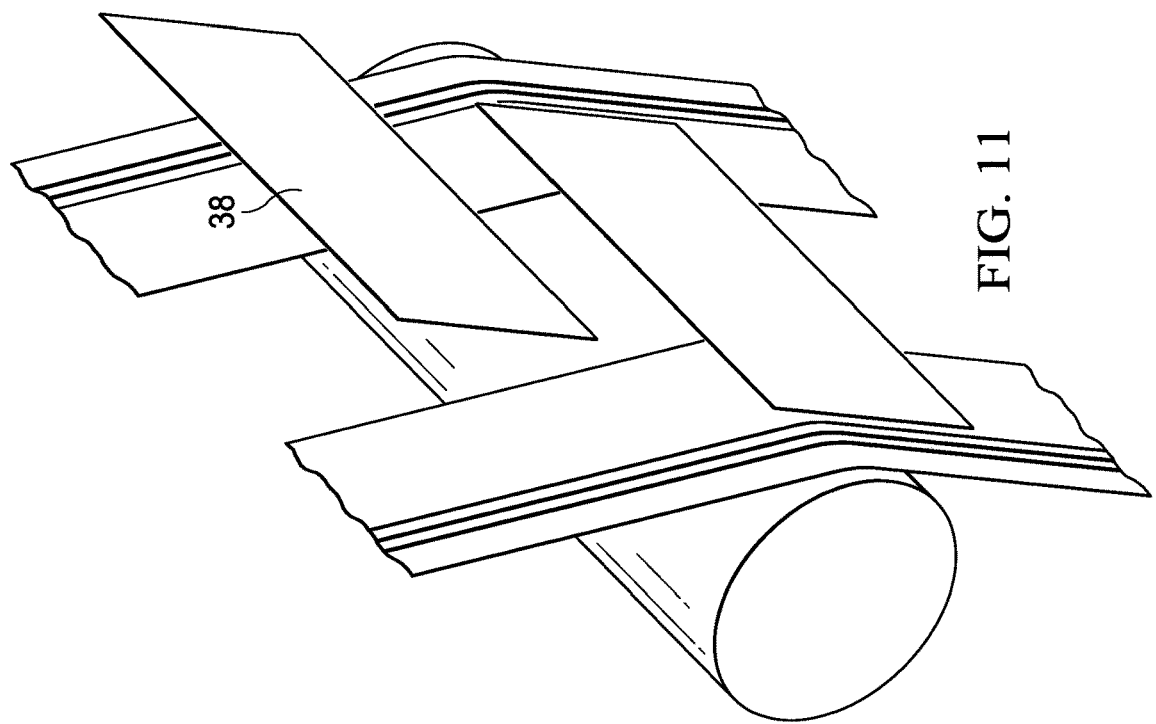
FIG. 11 is a schematic view of the central chassis joining step of the process of the present invention.

Referring to FIGS. 8 and 11, the thus obtained assembly is then sent to joining with the central chassis 38. The joining of the central chassis 38 may be provided by applying adhesive where the central chassis 38 is planned to be positioned. Adhesive may be provided in the entire region where the central chassis 38 overlaps, or in intervals. The positioning of the second group of elastic bodies 96SC may be selected such that the elastic body closest to the proximal edge of the first layer fold over of continuous sheet 93CS is disposed at a distance D6 away from the proximal edge of the first layer fold over of continuous sheet 93CS, wherein D6 may be at least about 5 mm. Referring to FIGS. 5-6, this may prevent any elastic body 96 from being accidentally left uncovered by the outer sheet fold over 93 in the finished article.

Preceding this step, referring to FIG. 12, the central chassis 38 may be formed by cutting a continuous central chassis 208 into discrete pieces, and processing through a transfer assembly 200. The transfer surface 236 of the transfer assembly 200 may pick up the central chassis 38 in a first position 216, turn the transfer surface 236 together with the central chassis 38 into a second position 218 while spacing the central chassis 38 as appropriate, and transferred to be joined such that the transverse axis of the central chassis 38 is aligned with the machine direction of the elastic belt making assembly. During the turning, the central chassis 38 may be held by the transfer surface 236 via vacuum. Upon transferring of the central chassis 38 from the transfer surface 236 to the assembly, vaccum is released, and instead the central chassis 38 is pressed onto the assembly for securely joining. In this assembling step, to avoid any transfer of adhesive glue or any other undesirable material to the transfer surface 236 from the central chassis 38 overlapping region of the assembly or from the second group of elastic bodies 96SC in the SEP, the second layer of continuous sheet 94CS may be planned to have a wider dimension in the cross machine direction than that of the central chassis 38 by more than 0 mm to no more than about 30 mm. Namely, in the resulting article, the distal edge of the second layer of continuous sheet which becomes the proximal edge of the inner sheet 94PE is distal than the distal edge of the central chassis 38DE as in FIGS. 3A-B. Alternatively, in the resulting article, the distal edge of the central chassis 38DE may be distal than the distal edge of the second layer of continuous sheet which becomes the proximal edge of the inner sheet 94PE as in FIGS. 5-7. For making the articles of FIGS. 5-7, joining of the central chassis 38 is carefully registered with the assembly in both the machine direction and the cross machine direction to avoid transfer of adhesive glue or any other undesirable material to the transfer surface 236.

Step D)

Figure 13:
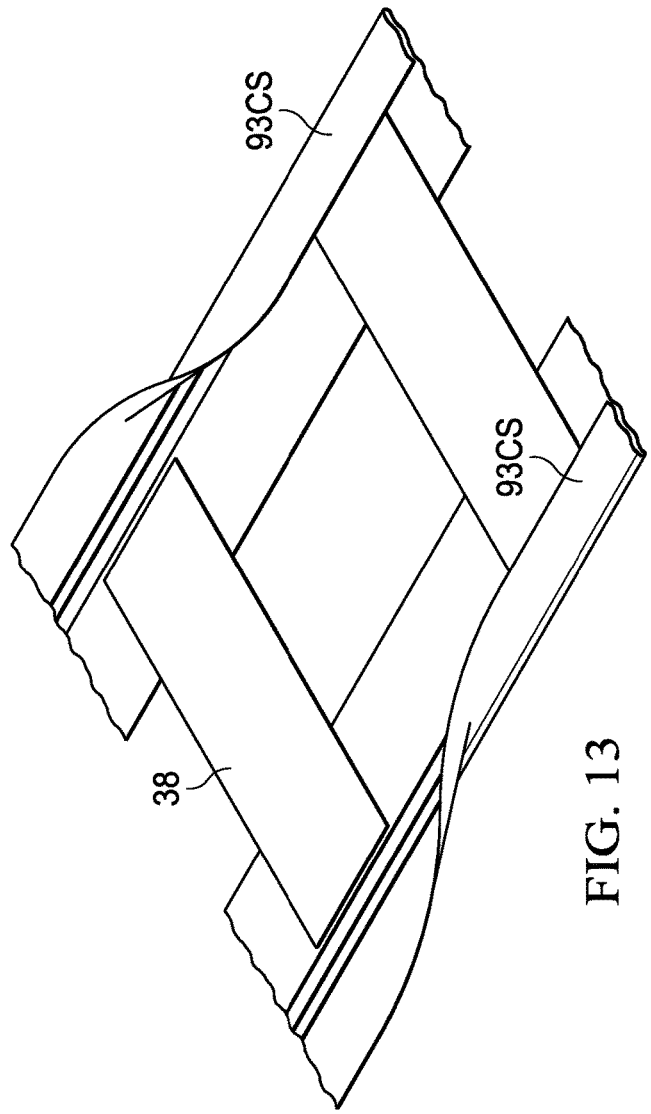
FIG. 13 is a schematic view of the first layer folding step of the process of the present invention.

Referring to FIG. 13, the obtained assembly is then sent to folding the first layer to form a first layer fold over of continuous sheet 93CS, such that at least one of the second group of elastic bodies 96SC is directly joined between the first surface of the first layer of continuous sheets 92CS and the first surface of the first layer fold over of continuous sheets 93CS.

As explained above, the second layer of continuous sheet 94CS may be planned to have a wider dimension in the cross machine direction than that of the central chassis 38. Further, the first layer fold over of continuous sheet 93CS may extend to overlap the central chassis 38. Referring to FIGS. 3A-B and 5-7, by taking such configuration in the SEP, the resulting article has the center chassis 38 securely sandwiched by at least the inner sheet 94 and the outer sheet fold over 93 in the vicinity of the longitudinal edge 38E by having an overlap D3 with the outer sheet fold over 93 in the longtitudinal direction, wherein D3 may be from about 10 mm to about 50 mm, or from about 10 mm to about 45 mm. Referring to FIGS. 3A-B and 5-7, in the resulting article, the inner sheet 94, however, does not extend to the distal edge 88 of the belt, thus, leaving some region where the belt is configured only by the outer sheet 92 and the outer sheet fold over 93. The inner belt distal edge 94DE may have a distance D4 from the belt distal edge 88, wherein D4 may be from about 10 mm to about 45 mm. By having such distance, meaningful cost saving of the inner sheet 94 is provided, while maintaining overall rigidity for the article. There may be at least 2 second group of elastic bodies 96SC, or from about 2 to about 8 second group of elastic bodies 96SC, or from about 2 to about 6 second group of elastic bodies per one side of the belt.

Further, referring to FIGS. 3C and 9, there may be a stiff region 37 in the FEP which is positioned in the resulting article towards the inner sheet distal edge 94DE wherein the outer sheet fold over 93, inner sheet 94, and outer sheet 92 overlap in the thickness direction. The stiff region 37 may overlap the absorbing material non-existing region 61 of the central chassis. By having many layers in this stiff region 37, rigidity and stiffness is provided to prevent bending. There is advantage to provide such stiffness in the stiff region 37, as this region tends to bend and thus may cause leakage during wear. For balancing the stiffness provided by this region while minimizing overlap of materials, the stiff region 37 is disposed of one to 4 elastics 96, or one to two elastics 96, and may have a longitudinal dimension of from about 6 mm to about 40 mm, or from about 6 mm to about 30 mm.

Figure 14:
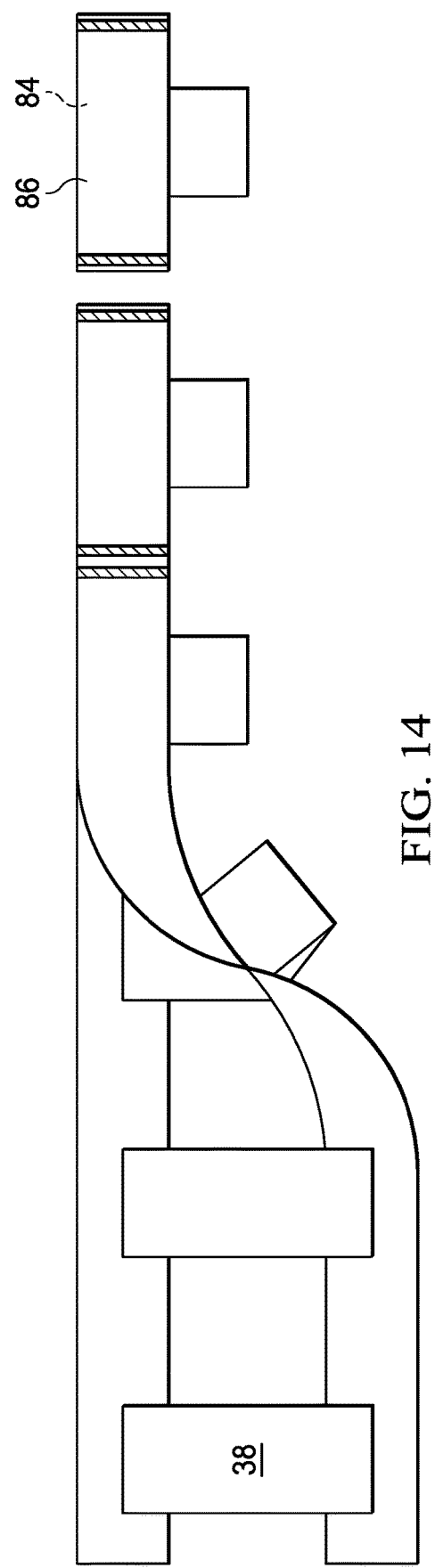
FIG. 14 is a schematic view of the central chassis folding, side seaming, and final cut steps of the process of the present invention.

Referring to FIG. 14, the thus obtained assembly is then folded at the middle point in the cross machine direction, seamed at the edges of the planned edges of the article, and then finally cut to obtain a wearable article.

Figure 15:
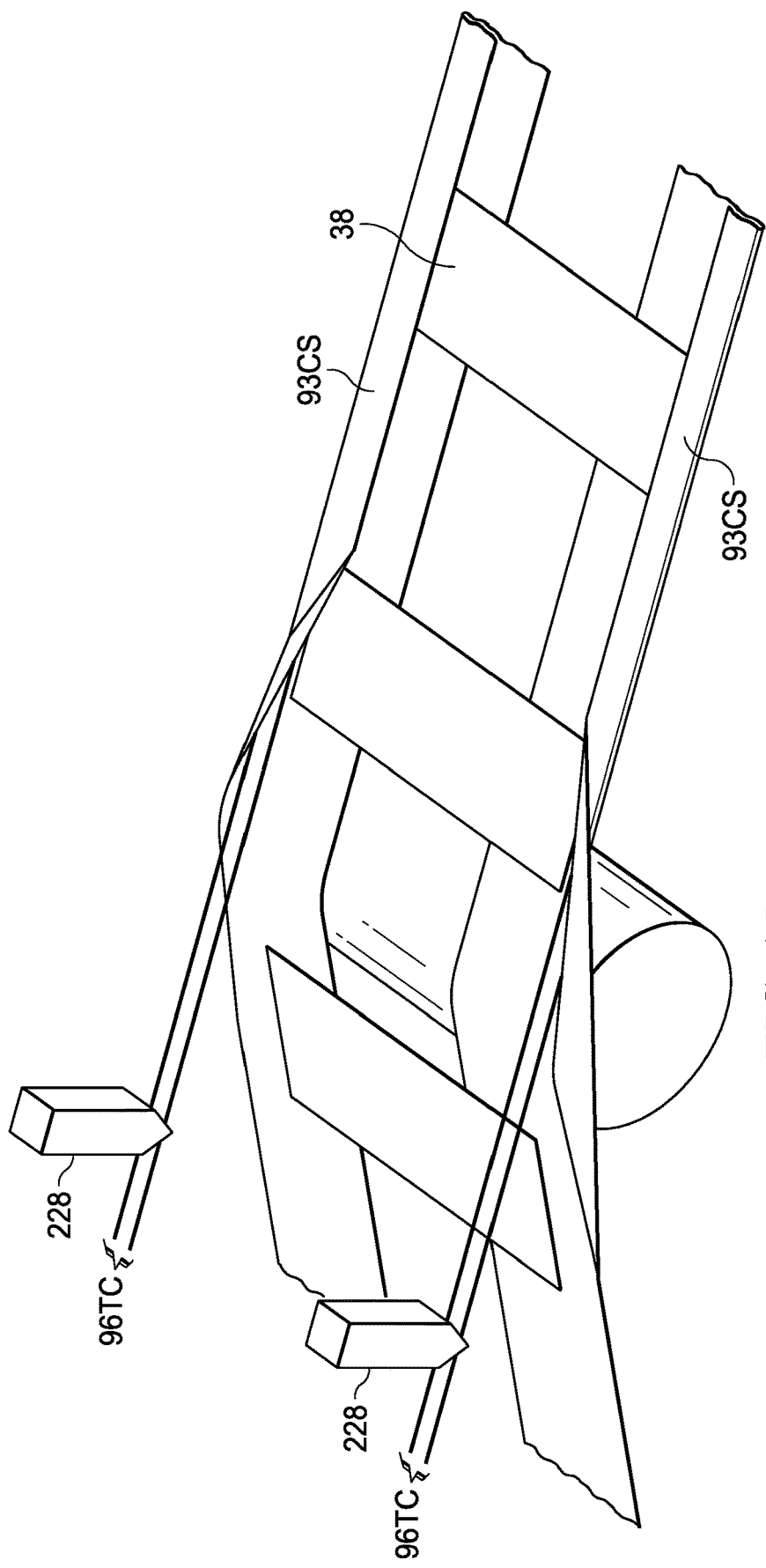
FIG. 15 is a schematic view of the third elastic bodies joining step of the process of the present invention.

Referring to FIG. 15, the present method may further comprise the steps, prior to Step D) of:

advancing the assembly in a machine direction;

advancing a third group of elastic bodies 96TC in the machine direction in a stretched state;

and then joining the third group of elastic bodies 96TC between the central chassis 38 and the first layer fold over of continuous sheet 93CS. The third group of elastic bodies may be introduced, for example, to overlap with the stiff region 37, and in a continuously elastic manner. Such elastic bodies may contribute to providing stiffness in the region to prevent bending in lieu of the second group of elastic bodies 96SC. Disposing elastic bodies closer to the wearer may be advantageous to provide closer fit.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a wearable article, comprising:
    assembling a front belt, a back belt, and a central chassis, the central chassis comprising a front waist region and a back waist region separated from each other by a crotch region, wherein at least one of the front belt and the back belt is formed by an elastic belt;
    making the elastic belt and joining to the central chassis by steps of:
        advancing a first layer of continuous sheet having a first surface and an opposing second surface in a machine direction and defining a width in a cross machine direction;
        advancing a second layer of continuous sheet having a first surface and an opposing second surface in the machine direction and having a smaller width than the first layer of continuous sheet;
        advancing at least one first group of elastic bodies in the machine direction in a stretched state;
        joining the at least one first group of elastic bodies between the first surface of the first layer and the first surface of the second layer of continuous sheet to form a primary elastic belt precursor;
        advancing at least one second group of elastic bodies in the machine direction in a stretched state;
        joining the at least one second group of elastic bodies to the first surface of the first layer of continuous sheet of the primary elastic belt precursor;
        joining the central chassis to the second surface of the second layer of continuous sheet;
        advancing at least one third group of elastic bodies in the machine direction in a stretched state; and
        folding the first layer of continuous sheet to form a first layer fold over of continuous sheet, such that at least one of the second group of elastic bodies is directly joined between the first surface of the first layer of continuous sheet and the first surface of the first layer fold over of continuous sheet, and such that the at least one third group of elastic bodies is joined between the central chassis and the first layer fold over of continuous sheet.

2. The method of claim 1, wherein a distal edge of the central chassis is distal relative to a distal edge of the second layer of continuous sheet.

3. A method of manufacturing a wearable article, comprising:
    assembling a front belt, a back belt, and a central chassis, the central chassis comprising a front waist region and a back waist region separated from each other by a crotch region, wherein at least one of the front belt and the back belt is formed by an elastic belt;
    making the elastic belt and joining to the central chassis by steps of:
        advancing a first layer of continuous sheet having a first surface and an opposing second surface in a machine direction and defining a width in a cross machine direction;
        advancing a second layer of continuous sheet having a first surface and an opposing second surface in the machine direction and having a smaller width than the first layer of continuous sheet;

advancing at least one first group of elastic bodies in the machine direction in a stretched state;

joining the at least one first group of elastic bodies between the first surface of the first layer and the first surface of the second layer of continuous sheet to form a primary elastic belt precursor;

joining the central chassis to the second surface of the second layer of continuous sheet of the primary elastic belt precursor;

advancing at least one second group of elastic bodies in the machine direction in a stretched state;

joining the at least one second group of elastic bodies to the first surface of the first layer of continuous sheet; and folding the first layer of continuous sheet to form a first layer fold over of continuous sheet, such that at least one of the second group of elastic bodies is directly joined between the first surface of the first layer of continuous sheet and the first surface of the first layer fold over of continuous sheet; and dividing the primary elastic belt precursor by a line along the machine direction to form a front primary elastic belt precursor and a back primary elastic belt precursor prior to joining the second group of elastic bodies with the first surface of the first layer of continuous sheet of the front primary elastic belt precursor or the back primary elastic belt precursor.

4. The method of claim 3, wherein at least a portion of the central chassis is joined between the first layer fold over and the second surface of the second layer of continuous sheets.

5. The method of claim 3, wherein a distal edge of the second layer of continuous sheet is distal relative to a distal edge of the central chassis.

6. The method of claim 3, wherein the front primary elastic belt precursor and the back primary elastic belt precursor are different in at least one of: a dimension of the front precursor, a dimension of the second precursor, a number of the at least one first group of elastic bodies, and positioning of the at least one first group of elastic bodies.

7. The method of claim 3, wherein the primary elastic belt precursor comprises an elastic region and a non-elastic region intermittently spaced apart in the machine direction.

8. The method of claim 7 wherein the non-elastic region is formed by leaving the at least one first group of elastic bodies disposed on the non-elastic region unjoined to adjacent sheets or joined with lower adhesion compared to remaining joined regions, followed by deactivating the elastic bodies disposed on the non-elastic region.

9. A method of manufacturing a wearable article, comprising:

assembling a front belt, a back belt, and a central chassis, the central chassis comprising a front waist region and a back waist region separated from each other by a crotch region;

making the front belt and the back belt and joining to the central chassis by steps of:

advancing a first layer of continuous sheet having a first surface and an opposing second surface in a machine direction and defining a width in a cross machine direction;

advancing a second layer of continuous sheet having a first surface and an opposing second surface in the machine direction and having a smaller width than the first layer of continuous sheet;

advancing a first group of elastic bodies in the machine direction in a stretched state;

joining the first group of elastic bodies between the first surface of the first layer and the first surface of the second layer of continuous sheet to form a primary elastic belt precursor, the primary elastic belt precursor comprising a non-elastic region formed by leaving a portion of the elastic bodies disposed on the non-elastic region unjoined to the first and second layers of continuous sheets;

dividing the primary elastic belt precursor by a line continuous in the machine direction to obtain a continuous front elastic belt precursor and a continuous back elastic belt precursor and deactivating the elastic bodies disposed on the non-elastic region of at least one of the continuous front elastic belt precursor and the continuous back elastic belt precursor;

advancing the continuous front elastic belt precursor and the continuous back elastic belt precursor in the machine direction;

advancing two sets of a second group of elastic bodies in the machine direction in a stretched state;

joining the second group of elastic bodies on the first surface of the first layer of each of the continuous front elastic belt precursor and the continuous back elastic belt precursor;

joining the front waist region of the central chassis to the non-elastic region of the continuous front elastic belt precursor and joining the back waist region of the central chassis to the non-elastic region of the continuous back elastic belt precursor; and folding the first layer of continuous sheets of each of the continuous front elastic belt precursor and the continuous back elastic belt precursor, to form a first layer fold over of continuous sheets, such that at least one of the second group of elastic bodies is directly joined between the first surface of the first layer of continuous sheets and the first surface of the first layer fold over of continuous sheets.

* * * * *